United States Patent [19]

Speelman et al.

[11] 4,384,583
[45] May 24, 1983

[54] TOURNIQUET

[75] Inventors: Irving A. Speelman, East Williston; James R. Hannah, Staten Island, both of N.Y.

[73] Assignee: Propper Manufacturing Co., Inc., Long Island City, N.Y.

[21] Appl. No.: 311,606

[22] Filed: Oct. 15, 1981

Related U.S. Application Data

[63] Continuation of Ser. No. 113,700, Jan. 21, 1980.

[51] Int. Cl.³ .............................................. A61B 17/12
[52] U.S. Cl. ........................................ 128/327; 2/338
[58] Field of Search .............. 128/327, 134, 133, 686, 128/DIG. 15; 2/DIG. 6, 338; 24/265 R

[56] References Cited

U.S. PATENT DOCUMENTS 3,086,529  4/1963  Munz et al. .................. 128/327
3,947,927  4/1976  Rosenthal .............. 128/DIG. 15 X Primary Examiner—Michael H. Thaler
Attorney, Agent, or Firm—Amster, Rothstein & Engelberg

[57] ABSTRACT

A tourniquet constructed from a length of elastic material. The ends of the elastic material are made non-elastic, and complementary coupling components are attached thereto. The elastic material is provided with a thickening for stress absorption and control.

4 Claims, 4 Drawing Figures

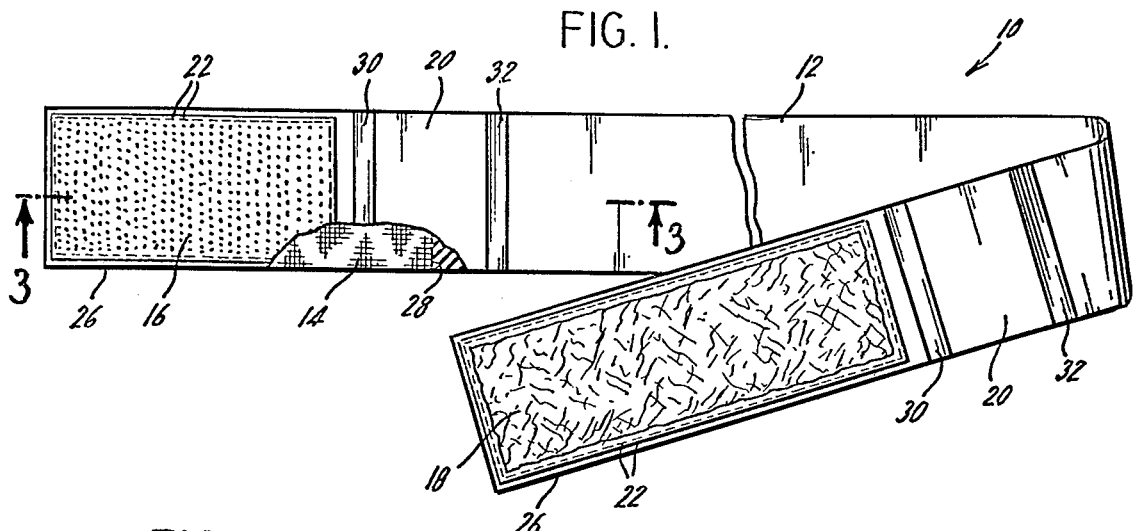
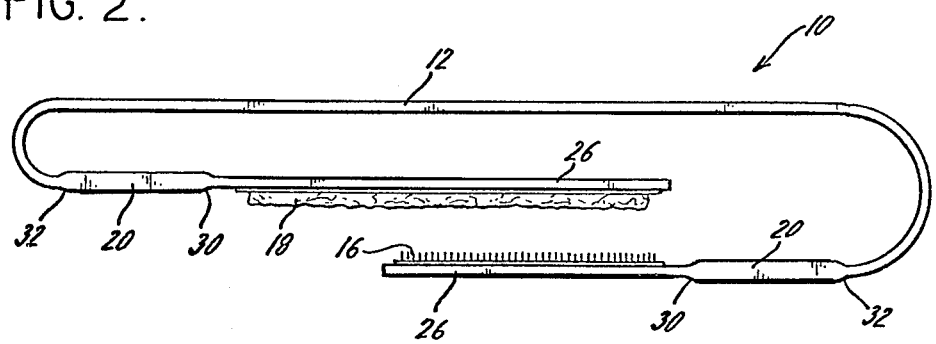
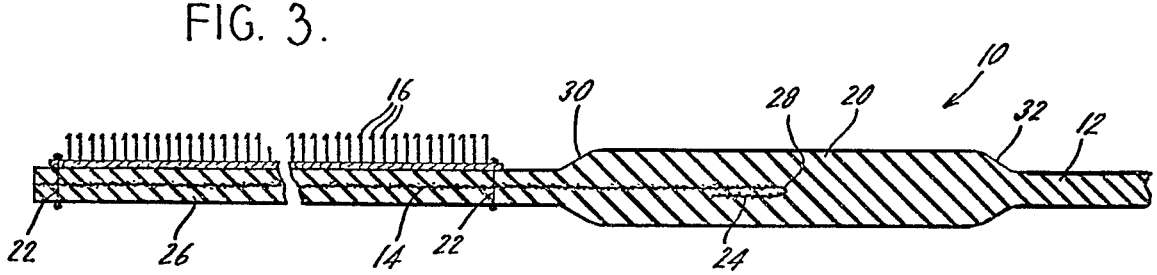
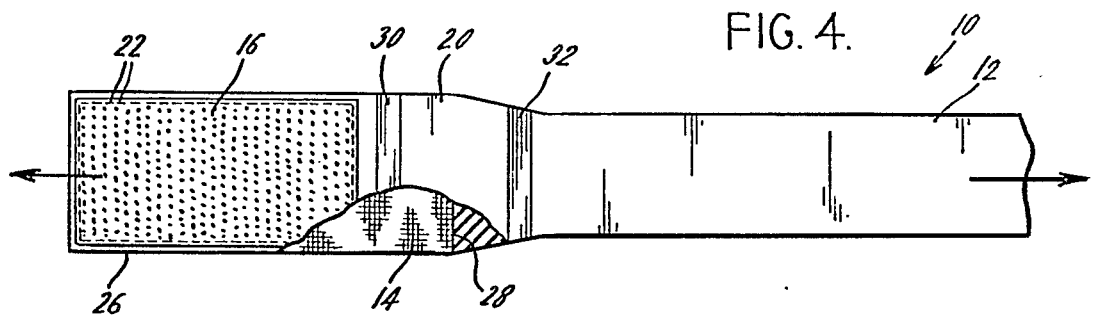

TOURNIQUET

This is a continuation, of application Ser. No. 113,700, filed Jan. 21, 1980.

This invention relates generally to a medical device and more particularly to a new and improved tourniquet.

Tourniquets find wide application in the medical field for the control of blood flow. Typical uses include: blood sampling procedures, in which a tourniquet is commonly applied to the patient's arm to create the distention of a vein to facilitate entry of a needle catheter; emergency procedures wherein it is necessary to control blood flow, such as after snake bite; and certain type of cardiac treatment where it is desired to control the circulation of blood in the body.

One type of tourniquet is described in U.S. Pat. No. 3,086,529 of Apr. 23, 1963 to N. M. Munz, et al. This tourniquet, however, suffers from several shortcomings which tend to limit its efficiency. In particular, there has been a marked tendency of such tourniquets to fail after repeated use. Such failure occurs at particular high stress points, and manifests itself as deterioration of the rubber from which the tourniquet is constructed.

It is an object of the present invention to provide a new and improved tourniquet which exhibits an extended life when compared to present tourniquets. It is a further object of the invention to provide a tourniquet having such extended life which is inexpensive and simple to manufacture.

The tourniquet of the present invention comprises a length of elastic material. The ends of the elastic material are made non-elastic, and complementary releaseable coupling components are attached thereto. The elastic material is thickened in the area of the inboard end of the non-elastic section, which thickening extends beyond the non-elastic section and provides a mechanism by which stretch induced stresses can be accommodated without elastic failure. Such an improved construction exhibits a markedly extended life to failure over the tourniquets of the prior art while remaining competitive on a cost basis.

The invention can be best understood from a consideration of the following detailed description, taken in connection with the accompanying drawings wherein:

FIG. 1 is a plan view of the tourniquet partially broken away showing the tourniquet coupling components and the inner structure of the tourniquet;

FIG. 2 is a longitudinal view of the tourniquet showing the orientation of the coupling components just prior to coupling;

FIG. 3 is a longitudinal section along line 3—3 of FIG. 1; and

FIG. 4 is a plan view of a section of the tourniquet when in a stressed configuration.

Referring more particularly to the drawings, tourniquet 10 comprises a strip of elastic material 12. Embedded within the ends of elastic material 12 are non-elastic strips 14, in this case of woven material. The ends of the elastic material 12 are further provided with complementary releaseable engagement coupling components 16 and 18. Thickening 20 is provided in elastic material 12 in the area of the inboard ends of non-elastic strips 14 for stress absorption and control. The inboard ends of non-elastic strips 14 may be folded back on themselves to further deter failure.

The strip of elastic material 12 of the tourniquet of FIGS. 1-4 can be conveniently manufactured from a strip of rubber, the exact choice of which is easily determined by one skilled in the art. The exact length, width, and thickness of the strip may be varied, depending on the ultimate purpose to which the tourniquet is to be employed, but a typical tourniquet of the present invention dimensioned for use on the human thigh would be approximately 12½" long by 1" wide by 1/16" in thickness in the unstressed configuration.

Embedded within the end sections 26 of the elastic material are inelastic strips 14. These strips are of any suitable relatively inexpensive material and may be conveniently constructed from a coarse-weave fabric material, the choice of which can be readily determined by those skilled in the art. The length of the inelastic strips 14 is chosen to be compatible with the length of complementary releaseable coupling components 16 and 18. Inelastic strips 14 both completely underlie coupling components 16 and 18, and extend inboard of the strips.

The inboard ends 28 of inelastic strips 14 may be folded back upon themselves, as illustrated in FIG. 3. This construction subjects folded edge 24 to the stress developed upon elongation and prevents unraveling of end 28 of the woven material 14. Such unraveling constituted a problem of the prior art tourniquet and often accompanied failure of the elastic material.

Complementary releasable coupling components 16 and 18 must have the ability to withstand repeated attachment and release and must be able to withstand the stresses produced parallel to the surface of the tourniquet when the tourniquet is in the applied, stressed configuration. Such complementary releaseable coupling components may preferably be those of the type sold under the trademark VELCRO which comprises a first component 16 having a mat of hook-like projections and a second component 18 comprising a pile. When components 16 and 18 are mated, the hooks of component 16 become enmeshed in the pile of component 18 and provide substantial holding power in directions parallel to their plane of attachment. Upon application of a force to the components in a direction perpendicular to their surfaces, however, the hook component readily disengages from the pile component, providing easy release. Pile component 18 should be long enough to permit connection with component 16 over a substantial length, to permit proper attachment around limbs of various circumferences. The length of hook component 16 is typically approximately 2½" long. It is to be noted that pile component 16 should be located on the face of the tourniquet lying upon the skin surface, while hook component 16 is located on the opposite face. This orientation prevents against possible skin irritation by the relatively stiff hook elements of hook component 16. Complementary releaseable coupling components 16 and 18 are connected to elastic material 12 by a perimeter line of stitching 22. Alternatively, other means of connection, such as adhesive or a vulcanization, are contemplated and may be utilized.

As previously stated, inelastic strips 14 underlie the entire length of coupling components 16 and 18 and extend a substantial distance inboard, as can be clearly seen in FIG. 3. This distance is chosen to focus stresses which develop at the elastic-inelastic interface at a point sufficiently away from the inboard ends of complementary releaseable coupling components 16 and 18 to avoid failure or distortion of these elements.

Inboard of both complementary releaseable coupling components 14 and 16 is thickening 20 of elastic material 12. This thickening, which can be easily seen in FIGS. 2 and 3, extends entirely across the width of elastic material 12 and runs from a point 30 inboard of the inner edge of the complementary releaseable coupling components 16 and 18 past the juncture of the inelastic sections and elastic sections of the tourniquet to a point 32 substantially inboard of the end of inelastic strips 14. This thickening is typically ⅛" in thickness. The length of the thickening is chosen to provide sufficient stress absorption and in the tourniquet illustrated in the figures may be approximately 1" in length.

The improved tourniquet of FIGS. 1-4 as previously described has shown a marked superiority over conventional tourniquets. Specifically, it has been found that after repeated flexure a typical conventional tourniquet, such as that disclosed in the Munz '529 patent, begins to deteriorate. This deterioration is most pronounced in the area abutting the connection means, where there is a transition from the elastic center section to the inelastic connection areas. In addition to the failure of the elastic strip, separation of the individual fibers of the inelastic strips has been observed. The design of the present invention, however, markedly increases the resistance of the tourniquet to such failures. For example, a 300% elongation stretch test run on sample tourniquets showed a mean life to failure of conventional tourniquets of 1,672 cycles, while the improved tourniquet of the present invention had a mean life to failure of over 3,500 cycles.

As can be seen in FIG. 4, the placing of tension on the tourniquet creates a narrowing of elastic material 12, as material must be displaced to provide the additional length. Thickened sections 20 provide a reservoir of material in the area of the ends of inelastic strips 14 and therefore permit elongation without substantial narrowing in the transverse direction. In addition, the added thickness increases the cross-sectional area of the tourniquet subject to stress and therefore decreases the resulting strain in that area.

Although the invention has been described as applied to a specific embodiment, it will be clear that many modifications may be performed within the scope of the invention claimed.

We claim:

1. A tourniquet adapted to encircle a limb with opposite end portions of said tourniquet overlapping one another to form a closed band around said limb comprising a strip of elastic material, said strip including a center section and two end sections, said end sections being reinforced with an inelastic material embedded in said elastic material at said end sections to render said end sections relatively inelastic, said inelastic material having an inboard edge, complementary releaseable coupling means secured to said end sections, the elastic material of said center section and said end sections being thickened at their juncture to provide a section of thickened elastic material extending at least a relatively short distance on either side of the inboard edge of said inelastic material to reduce the likelihood of failure of said elastic material proximate to said center section-end section junctures.

2. The tourniquet of claim 1, wherein the inboard edge of said inelastic material is so constructed and arranged to be fray-free.

3. The tourniquet of claim 1, wherein said inelastic strips are folded back upon themselves to reinforce the inboard edge thereof.

4. A tourniquet adapted to encircle a limb with opposite end portions of said tourniquet overlapping one another to form a closed band around said limb comprising a strip of elastic material, said strip including a center section and two end sections, said end sections being reinforced with an inelastic material embedded in said elastic material at said end sections to render said end sections relatively inelastic, complementary releaseable coupling means secured to said end sections, the elastic material of said center section and said end sections being thickened above and below said inelastic material for at least a relatively short distance on either side of the inboard edge of said inelastic material to form a thickened unitary portion of said strip to provide a reservoir of material communicating with said center portion to reduce the likelihood of failure of said elastic material proximate to said center section-end section junctures.

* * * * *